United States Patent [19]

Fuchs et al.

[11] Patent Number: 5,739,324
[45] Date of Patent: Apr. 14, 1998

[54] PREPARATION OF CAPROLACTAM

[75] Inventors: Eberhard Fuchs, Frankenthal; Tom Witzel, Ludwigshafen, both of Germany

[73] Assignee: BASF Aktiengesellschaft, Ludwigshafen, Germany

[21] Appl. No.: 646,279

[22] PCT Filed: Nov. 16, 1994

[86] PCT No.: PCT/EP94/03781

§ 371 Date: May 15, 1996

§ 102(e) Date: May 16, 1996

[87] PCT Pub. No.: WO95/14664

PCT Pub. Date: Jun. 1, 1995

[30] Foreign Application Priority Data

Nov. 20, 1993 [DE] Germany .................. 43 39 648.8

[51] Int. Cl.⁶ .................. C07D 201/08; C07D 223/10

[52] U.S. Cl. .................. 540/539; 540/220; 540/451; 540/482; 546/243; 548/486; 548/553

[58] Field of Search .................. 540/200, 451, 540/482, 539; 546/243; 548/486, 553

[56] References Cited

U.S. PATENT DOCUMENTS 4,625,023  11/1986  Mares et al. .................. 540/539
4,628,085  12/1986  Mares et al. .................. 540/539

*Primary Examiner*—John M. Ford
*Assistant Examiner*—Pavanaram K. Sripada
*Attorney, Agent, or Firm*—Keil & Weinkauf

[57] ABSTRACT

A process for preparing cyclic lactams by reacting amino carbonitriles with water in liquid phase in the presence of heterogeneous catalysts based on titanium dioxide, zirconium oxide, cerium oxide and aluminum oxide.

6 Claims, No Drawings

PREPARATION OF CAPROLACTAM

This is a 371 of PCT/EP94/03781, filed 15 Nov. 1994, which claims priority of German Application P 4339648.8, filed 20 Nov. 1993.

The present invention relates to a novel process for preparing cyclic lactams by reacting amino carbonitriles with water in the presence of catalysts.

U.S. Pat. No. 4,628,085 discloses the reaction of 6-aminocapronitrile with water in the gas phase on acidic silica gel at 300° C. The reaction takes place quantitatively with an initial selectivity of 95% to produce caprolactam, but the productivity and selectivity are found to decline rapidly. A similar process is described in U.S. Pat. No. 4,625,023, in which a highly diluted gas stream composed of 6-aminocapronitrile, adiponitrile, ammonia, water and carrier gas is passed over a silica gel catalyst bed and a copper/chromium/barium/titanium oxide catalyst bed. Caprolactam is obtained with a selectivity of 91% and a conversion of 85%. In this case too there is rapid inactivation of the catalyst.

U.S. Pat. No. 2,301,964 relates to the uncatalyzed conversion of 6-aminocapronitrile to caprolactam in aqueous solution at 285° C. The yields are below 80%.

FR-A 2 029 540 describes a process for cyclization of 6-aminocapronitrile to caprolactam using homogeneous metal catalysts from the zinc and copper group in aqueous solution, caprolactam being obtained in yields of up to 83%. However, there are problems in complete removal of the catalyst from the required caprolactam because the latter forms complexes with the metals used.

It is an object of the present invention to provide a process for preparing cyclic lactams by reacting amino carbonitriles with water which does not entail the disadvantages described above.

We have found that this object is achieved by carrying out the reaction in liquid phase in the presence of heterogeneous catalysts based on titanium dioxide, zirconium oxide, cerium oxide and aluminum oxide.

Preferred embodiments of the process according to the invention are evident from the dependent claims.

The starting materials employed in the process according to the invention are amino carbonitriles, preferably those of the general formula I

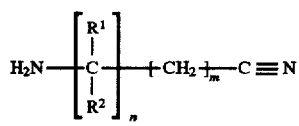

where n and m are each 0, 1, 2, 3, 4, 5, 6, 7, 8 or 9, and n+m total at least 3, preferably at least 4.

$R^1$ and $R^2$ can, in principle, be substituents of any type, it merely being necessary to ensure that the required cyclization is unaffected by the substituents. $R^1$ and $R^2$ are preferably, independently of one another, each $C_1$–$C_6$-alkyl, $C_5$–$C_7$-cycloalkyl or $C_6$–$C_{12}$-aryl.

Particularly preferred starting compounds are amino carbonitriles of the general formula

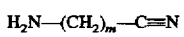

where m is 3, 4, 5 or 6, in particular 5. The starting compound when m=5 is 6-aminocapronitrile.

In the process according to the invention, the amino carbonitriles described above are reacted with water in liquid phase using heterogeneous catalysts to give cyclic lactams. Use of amino carbonitriles of the formula I results in the corresponding cyclic lactams of the formula II

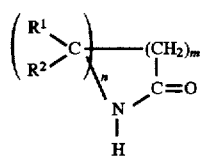

where n, m, $R^1$ and $R^2$ have the abovementioned meanings. Particularly preferred lactams are those where n is 0 and m is 4, 5 or 6, in particular 5 (in the latter case, caprolactam is obtained).

The reaction is carried out in liquid phase at, in general, from 140° to 320° C., preferably 160° to 280° C.; the pressure is generally in the range from 1 to 250 bar, preferably from 5 to 150 bar, it being necessary to ensure that the reaction mixture is predominantly liquid under the conditions employed. The holdup times are generally in the range from 1 to 120, preferably 1 to 90 and, in particular, 1 to 60 min. In some cases, holdup times of 1–10 min have proved to be entirely sufficient.

In general, at least 0.01 mol, preferably 0.1–20 mol and, in particular, 1–5 mol of water are employed per mol of amino carbonitrile.

The amino carbonitrile is advantageously employed in the form of a 1–50% by weight, in particular 5–50% by weight, particularly preferably 5–30% by weight, solution in water (in which case the solvent is also reactant) or in water/solvent mixtures. Examples of solvents which may be mentioned are alkanols such as methanol, ethanol, n- and i-propanol, n-, i- and t-butanol and polyols such as diethylene glycol and tetraethylene glycol, hydrocarbons such as petroleum ether, benzene, toluene, xylene, lactams such as pyrrolidone or caprolactam, or alkyl-substituted lactams such as N-methylpyrrolidone, N-methylcaprolactam or N-ethylcaprolactam, as well as esters of carboxylic acids with, preferably, 1–8 carbon atoms. Ammonia can also be present in the reaction. Mixtures of organic solvents can, of course, also be used. Mixtures of water and alkanols in the water/alkanol ratio by weight of 1–75/25–99, preferably 1–50/50–99, have emerged in some cases as particularly advantageous.

Catalysts which, under the reaction conditions described above, have very high conversions, yields, selectivities and useful lives are heterogeneous catalysts based on titanium oxide, zirconium oxide, cerium oxide and aluminum oxide. These can be used in the form of powders, granules, chips, pellets or tablets. The form required for the oxides generally depends on the requirements of the particular reaction procedure, using powder or granules in suspension. In a fixed bed procedure, tablets or pellets with diameters of from 1 mm to 10 mm are normally used.

Aluminum oxide is suitable in all modifications which can be obtained by heating the precursor aluminum hydroxide (gibbsite, boehmite, pseudoboehmite, bayerite and diaspore) at various temperatures. These include in particular gamma- and alpha-aluminum oxide and mixtures thereof.

The oxides can be used in pure form (>80% by weight content of the particular oxide), as mixture of the abovementioned oxides, in which case the total of the abovementioned oxides should be >80% by weight, or as supported catalyst, in which case the abovementioned oxides can be applied to a mechanically and chemically stable support, usually with a large surface area.

The pure oxides can have been prepared by precipitation from aqueous solutions, eg. titanium dioxide by the sulfate process, or by other processes, eg. the pyrogenic production of fine aluminum oxide, titanium dioxide or zirconium dioxide powders, which are commercially available.

Several methods are available for preparing mixtures of the various oxides. The oxides, or their precursors which can be converted into the oxides by calcination, can be prepared, for example, by coprecipitation from solution. This generally results in very good dispersion of the two oxides used. The oxide or precursor mixtures can also be prepared by precipitating the one oxide or precursor in the presence of the second oxide or precursor which is present as suspension of finely dispersed particles. Another method comprises mechanically mixing the oxide or precursor powders, and this mixture can be used as starting material for preparing pellets or tablets.

Various methods are available for preparing supported catalysts. Thus, for example, the oxides can be applied in the form of their sols to the support by simple impregnation. Drying and calcination are normally carried out to remove the volatile constituents of the sol from the catalyst. Sols of titanium dioxide, aluminum oxide and zirconium dioxide are commercially available.

Another possibility for applying layers of active oxides comprises hydrolysis or pyrolysis of organic or inorganic compounds. Thus, a ceramic support can be coated with titanium dioxide in a thin layer by hydrolyzing titanium isopropoxide or other titanium alkoxides. Other suitable compounds include $TiCl_4$, zirconyl chloride, aluminum nitrate and cerium nitrate. Suitable supports are powders, extrudates or tablets of the said oxides themselves or other stable oxides such as silicon dioxide. The supports can be made macroporous to improve transport of matter.

The process according to the invention results in cyclic lactams, in particular caprolactam, in high yield with good selectivities and good maintenance of catalyst activity.

EXAMPLES

Examples 1 to 6

A solution of 6-aminocapronitrile (ACN) in water and ethanol in the ratios by weight stated in the table was passed under 100 bar into a heated tubular reactor with a capacity of 25 ml (diameter 6 mm, length 800 mm) which was packed with titanium dioxide (anatase) in the form of 1.5 mm pellets. The product stream leaving the reactor was analyzed by gas chromatography and high-pressure liquid chromatography (HPLC). The results are likewise to be found in the table.

TABLE

| Ex. | ACN [% by wt.] | Water [% by wt.] | ACN/$H_2O$ molar ratio [%] [sic] | Ethanol [% by weight] | Temp. [°C.] | Holdup time [min] | Conversion [%] | Sel. [%] |
|---|---|---|---|---|---|---|---|---|
| 1 | 10 | 6.4 | 1:4 | 83.6 | 180 | 30 | 90 | 98 |
| 2 | 10 | 6.4 | 1:4 | 83.6 | 200 | 30 | 100 | 88 |
| 3 | 10 | 6.4 | 1:4 | 83.6 | 220 | 30 | 100 | 94 |
| 4 | 10 | 6.4 | 1:4 | 83.6 | 240 | 30 | 100 | 88 |
| 5 | 15 | 9.6 | 1:4 | 75.4 | 220 | 30 | 100 | 86 |
| 6 | 10 | 1.6 | 1:1 | 88.4 | 220 | 30 | 99 | 93 |

Comparative Test

A solution of 10% aminocapronitrile, 6.4% water and 83.6% ethanol was reacted as in the tests described in Example 1 without a heterogeneous catalyst at 250° C. with a holdup time of 30 min in an empty tubular reactor. The conversion was 28% and the selectivity for caprolactam was 74%.

Examples 7 to 16

Examples 7 to 16 were carried out as in Examples 1 to 6 using the same tubular reactor and employing 13.3 g of $TiO_2$

TABLE

| Ex. | Cat. | Solvent | Temp. [°C.] | Water/ACN [mol/mol] | Feed rate [ml/h] | Free volume [ml] | HUT [min] | Conv. [%] | Sel. [%] |
|---|---|---|---|---|---|---|---|---|---|
| 7 | $TiO_2$ | EtOH | 180 | 2 | 9.3 | 9.3 | 60 | 96 | 92 |
| 8 | $TiO_2$ | EtOH | 230 | 2 | 62 | 9.3 | 9 | 100 | 91 |
| 9 | $TiO_2$ | EtOH | 260 | 2 | 139.5 | 9.3 | 4 | 99 | 91 |
| 10 | $TiO_2$ | EtOH | 180 | 4 | 9.3 | 9.3 | 60 | 98 | 93 |
| 11 | $TiO_2$ | EtOH | 230 | 4 | 80 | 9.3 | 7 | 92 | 94 |
| 12 | $TiO_2$ | EtOH | 230 | 4 | 56 | 9.3 | 10 | 100 | 90 |
| 13 | $TiO_2$ | EtOH | 260 | 4 | 139.5 | 9.3 | 4 | 98 | 91 |
| 14 | $TiO_2$ | EtOH | 180 | 10 | 9.3 | 9.3 | 60 | 98 | 91 |
| 15 | $TiO_2$ | EtOH | 230 | 10 | 56 | 9.3 | 10 | 97 | 93 |
| 16 | $TiO_2$ | EtOH | 260 | 10 | 62 | 9.3 | 9 | 100 | 93 |

Examples 17 to 22

Examples 17 to 22 were carried out as in Examples 1 to 6 using the same tubular reactor and employing 20 g of $TiO_2$

TABLE

| Ex. | Cat. | Solvent | Temp. [°C.] | Water/ACN [mol/mol] | Feed rate [ml/h] | Free volume [ml] | HUT [min] | Conv. [%] | Sel. [%] |
|---|---|---|---|---|---|---|---|---|---|
| 17 | $TiO_2$ | MeOH | 220 | 2 | 29 | 14.2 | 30 | 100 | 91 |
| 18 | $TiO_2$ | EtOH | 220 | 2 | 29 | 14.2 | 30 | 100 | 89 |
| 19 | $TiO_2$ | n-PrOH | 220 | 2 | 29 | 14.2 | 30 | 100 | 79 |
| 20 | $TiO_2$ | i-PrOH | 220 | 2 | 29 | 14.2 | 30 | 100 | 87 |
| 21 | $TiO_2$ | n-BuOH | 220 | 2 | 29 | 14.2 | 30 | 100 | 81 |
| 22 | $TiO_2$ | TEG | 220 | 2 | 29 | 14.2 | 30 | 99 | 89 |

TEG = tetraethylene glycol

Examples 23 to 27

Examples 23 to 27 were carried out as in Examples 1 to 6 using the same tubular reactor and employing different catalysts.

TABLE

| Ex. | Cat. | Solvent | Temp. [°C.] | Water/ACN [mol/mol] | Feed rate [ml/h] | Free volume [ml] | HUT [min] | Conv. [%] | Sel. [%] |
|---|---|---|---|---|---|---|---|---|---|
| 23 | $ZrO_2$ | EtOH | 220 | 2 | 27 | 13.3 | 30 | 90 | 83 |
| 24 | $\gamma\text{-}Al_2O_3$ | EtOH | 240 | 4 | 27 | 13.6 | 30 | 84 | 91 |
| 25 | $\gamma\text{-}Al_2O_3$ | EtOH | 260 | 4 | 27 | 13.6 | 30 | 97 | 93 |
| 26 | $\alpha\text{-}Al_2O_3$ | EtOH | 240 | 4 | 25 | 12.6 | 30 | 91 | 84 |
| 27 | $CeO_2$ | EtOH | 220 | 4 | 20 | 10.3 | 30 | 100 | 90 |

TABLE

| Ex. | Cat. | Solvent | Temp. [°C.] | Water/ACN [mol/mol] | Feed rate [ml/h] | Free volume [ml] | HUT [min] | Conv. [%] | Sel. [%] |
|---|---|---|---|---|---|---|---|---|---|
| 28 | $ZrO_2$ | EtOH | 220 | 2 | 27 | 13.3 | 30 | 90 | 83 |
| 28 | $\gamma\text{-}Al_2O_3$ | EtOH | 240 | 4 | 27 | 13.6 | 30 | 84 | 91 |
| 30 | $\gamma\text{-}Al_2O_3$ | EtOH | 260 | 4 | 27 | 13.6 | 30 | 97 | 93 |
| 31 | $\alpha\text{-}Al_2O_3$ | EtOH | 240 | 4 | 25 | 12.6 | 30 | 91 | 84 |
| 32 | $CeO_2$ | EtOH | 220 | 4 | 20 | 10.3 | 30 | 100 | 90 |

We claim:

1. A process for preparing cyclic lactams by reacting amino carbonitriles with water in the presence of catalysts, wherein the reaction is carried out in liquid phase in the presence of heterogeneous catalysts based on titanium dioxide, zirconium oxide, cerium oxide and aluminum oxide.

2. A process as defined in claim 1, wherein the reaction is carried out at from 140° to 320° C.

3. A process as defined in claim 1, wherein amino carbonitriles of the formula

$$H_2N\text{---}(CH_2)_m\text{---}C\equiv N$$

where m is 3, 4, 5 or 6 are employed.

4. A process as defined in claim 3, wherein 6-aminocapronitrile is employed as amino carbonitrile.

5. A process as defined in claim 1, wherein a 1–50% by weight solution of the amino carbonitrile in water or in water/organic solvent mixtures is employed.

6. A process as defined in claim 4, wherein the reaction is carried out at from 160° to 180° C. at a pressure of from 5 to 150 bar.

* * * * *

UNITED STATES PATENT AND TRADEMARK OFFICE
CERTIFICATE OF CORRECTION

PATENT NO.: 5,739,324

DATED: April 14, 1998

INVENTOR(S): FUCHS et al.

It is certified that error appears in the above-identified patent and that said Letters Patent is hereby corrected as shown below:

On the cover page, item [22], "Nov. 16, 1994" should be --Nov. 15, 1994--.

On the cover page, item [86], "May 15, 1996" should be --May 16, 1996--.

Signed and Sealed this

Seventh Day of July, 1998

*Attest:*

BRUCE LEHMAN

*Attesting Officer*     *Commissioner of Patents and Trademarks*